United States Patent
Gilbert et al.

(10) Patent No.: US 9,839,470 B2
(45) Date of Patent: Dec. 12, 2017

(54) ELECTROSURGICAL GENERATOR FOR MINIMIZING NEUROMUSCULAR STIMULATION

(71) Applicant: COVIDIEN LP, Mansfield, MA (US)

(72) Inventors: James A. Gilbert, Boulder, CO (US); Daniel A. Friedrichs, Aurora, CO (US)

(73) Assignee: COVIDIEN LP, Mansfield, MA (US)

( * ) Notice: Subject to any disclaimer, the term of this patent is extended or adjusted under 35 U.S.C. 154(b) by 120 days.

(21) Appl. No.: 14/754,855

(22) Filed: Jun. 30, 2015

(65) Prior Publication Data

US 2017/0000549 A1   Jan. 5, 2017

(51) Int. Cl.
*A61B 18/12* (2006.01)
*H02M 7/5387* (2007.01)
(Continued)

(52) U.S. Cl.
CPC ..... *A61B 18/1233* (2013.01); *H02M 7/53871* (2013.01); *A61B 18/1402* (2013.01);
(Continued)

(58) Field of Classification Search
CPC ............ A61B 18/1206; A61B 18/1233; A61B 2018/1253; A61B 2018/126; A61B 18/1402; A61B 18/1445; A61B 2018/00642; A61B 2018/00702; A61B 2018/00726; A61B 2018/00732; A61B 2018/00761; A61B 2018/00779; A61B 2018/00791; A61B 2018/00827; A61B 2018/00875; A61B 2018/00892;
(Continued)

(56) References Cited

U.S. PATENT DOCUMENTS

| 4,188,927 A | 2/1980 | Harris |
| 5,472,443 A * | 12/1995 | Cordis ............... A61B 18/1206 606/32 |
| 6,618,626 B2 | 9/2003 | West, Jr. et al. |
| 7,226,447 B2 | 6/2007 | Uchida et al. |

(Continued)

FOREIGN PATENT DOCUMENTS

| EP | 2777578 A1 | 9/2014 |
| EP | 2826433 A2 | 1/2015 |
| WO | 2011084957 A1 | 7/2011 |

OTHER PUBLICATIONS

European Search Report for corresponding EP Application No. 16 17 6914, dated Oct. 31, 2016, 8 pages.
(Continued)

*Primary Examiner* — Daniel Fowler
*Assistant Examiner* — Sean W Collins

(57) ABSTRACT

A system for minimizing neuromuscular stimulation includes a converter, an inverter, and a controller. The converter is configured to output a dc waveform and includes at least one first switching element operated at a first duty cycle. The inverter is coupled to the converter and includes at least one second switching element operated at a second duty cycle. The inverter is configured to invert the DC waveform to generate an electrosurgical pulse waveform. The controller is coupled to the converter and the inverter, and is configured to control the first duty cycle to adjust a magnitude of the electrosurgical pulse waveform and the second duty cycle to adjust at least one property of the electrosurgical pulse waveform to minimize neuromuscular stimulation.

19 Claims, 7 Drawing Sheets

(51) Int. Cl.
*A61B 18/14* (2006.01)
*A61B 18/00* (2006.01)
*H02M 1/00* (2006.01)

(52) U.S. Cl.
CPC . *A61B 18/1445* (2013.01); *A61B 2018/00642* (2013.01); *A61B 2018/00702* (2013.01); *A61B 2018/00726* (2013.01); *A61B 2018/00732* (2013.01); *A61B 2018/00761* (2013.01); *A61B 2018/00779* (2013.01); *A61B 2018/00791* (2013.01); *A61B 2018/00827* (2013.01); *A61B 2018/00875* (2013.01); *A61B 2018/00892* (2013.01); *A61B 2018/126* (2013.01); *A61B 2018/1253* (2013.01); *A61B 2018/1286* (2013.01); *H02M 2001/007* (2013.01)

(58) Field of Classification Search
CPC .... A61B 2018/1286; H02M 2001/007; H02M 7/53871
See application file for complete search history.

(56) References Cited

U.S. PATENT DOCUMENTS

| | | | |
|---|---|---|---|
| 7,846,156 B2 | 12/2010 | Malis et al. | |
| 7,862,560 B2 | 1/2011 | Marion | |
| 2007/0066971 A1 | 3/2007 | Podhajsky | |
| 2010/0324611 A1* | 12/2010 | Deming | A43B 3/0005 607/2 |
| 2012/0215216 A1* | 8/2012 | Friedrichs | A61B 18/1206 606/38 |
| 2012/0220999 A1* | 8/2012 | Long | A61B 18/1206 606/41 |
| 2014/0052126 A1* | 2/2014 | Long | A61B 18/1206 606/34 |
| 2015/0032096 A1 | 1/2015 | Johnson | |

OTHER PUBLICATIONS

Japanese Office Action dated May 18, 2017 issued in corresponding Japanese Application No. 2016-127423.

* cited by examiner

ELECTROSURGICAL GENERATOR FOR MINIMIZING NEUROMUSCULAR STIMULATION

BACKGROUND

Technical Field

The present disclosure relates to electrosurgical apparatuses and methods for minimizing neuromuscular stimulation. More particularly, the present disclosure relates to a method and apparatus for adjusting frequencies of electrosurgical waveforms generated by an electrosurgical generator to minimize neuromuscular stimulation.

Background of Related Art

Electrosurgery involves application of high radio frequency electrical current to a surgical site to cut, thermally or non-thermally ablate, or coagulate tissue. In monopolar electrosurgery, a source or active electrode delivers radio frequency alternating current from the electrosurgical generator to the targeted tissue. A patient return electrode is placed remotely from the active electrode to conduct the current back to the generator.

In bipolar electrosurgery, return and active electrodes are placed in close proximity to each other such that an electrical circuit is formed between the two electrodes (e.g., in the case of an electrosurgical forceps). In this manner, the applied electrical current is limited to the body tissue positioned between the electrodes. Accordingly, bipolar electrosurgery generally involves the use of instruments where it is desired to achieve a focused delivery of electrosurgical energy between two electrodes positioned on the instrument, e.g. forceps or the like.

When electrosurgical energy is generated, a frequency component is included in the generated electrosurgical waveform. If a large amount of electrosurgical energy is present at a low frequency of about 100 kilo hertz (kHz) or less, the electrosurgical waveform may stimulate muscle tissue and/or nerves. Muscle and nerve stimulation may be prevented by employing neuromuscular blocking agents (NMBAs) or such stimulation may be used to identify muscles or nerves by using neuromuscular stimulation agents (NMSAs). However, use of NMSAs or NMBAs is undesirable as these agents may produce an allergic reaction and/or may result in insufficient or overly aggressive paralysis of muscles and/or nerves of a patient. Thus, there is a need for electrosurgical generators minimizing the need for NMSAs and NMBAs.

SUMMARY

The present disclosure provides an electrosurgical apparatus, which adjusts frequency components of electrosurgical energy such that a large amount of electrosurgical energy is present at the adjusted frequency, which is higher than frequencies that may stimulate muscles and nerves. This allows for reducing the need for NMSAs and NMBAs, which may be potentially harmful as described above.

In an embodiment, a system for minimizing neuromuscular stimulation includes a converter, an inverter, and a controller. The converter is configured to output a dc waveform and includes at least one first switching element operated at a first duty cycle. The inverter is coupled to the converter and includes at least one second switching element operated at a second duty cycle. The inverter is configured to invert the DC waveform to generate an electrosurgical pulse waveform. The controller is coupled to the converter and the inverter, and is configured to control the first duty cycle to adjust a magnitude of the electrosurgical pulse waveform and the second duty cycle to adjust at least one property of the electrosurgical pulse waveform.

In an aspect, the electrosurgical pulse waveform is monophasic to cause neuromuscular stimulation, and the at least one property includes at least one of a repetition frequency or a pulse width period. The controller is further configured to adjust the repetition frequency of the monophasic electrosurgical pulse waveform to be greater than about 100 kHz. In another aspect, the controller is further configured to adjust the pulse width period of the electrosurgical pulse waveform to be less than about 2 µs.

In another aspect, the electrosurgical pulse waveform is biphasic to reduce an amount of an NMBA, and the at least one property includes at least one of a repetition frequency or a pulse width period. The controller is further configured to adjust the repetition frequency of the biphasic electrosurgical pulse waveform to be greater than about 100 kHz. In another aspect, the controller is further configured to adjust the pulse width period of each cycle of the biphasic electrosurgical pulse waveform such that a highest amplitude peak of the biphasic electrosurgical pulse waveform is present from about 500 kHz to about 5 MHz in a frequency domain.

In yet another aspect, the converter is a buck converter or the inverter is a boost converter.

In another embodiment, a method for controlling an electrosurgical generator to minimize neuromuscular stimulation includes operating at least one first switching element of a converter of the electrosurgical generator at a first duty cycle to output a DC waveform, operating at least one second switching element of an inverter of the electrosurgical generator at a second duty cycle to convert the DC waveform to generate an electrosurgical pulse waveform, and controlling the first duty cycle to adjust a magnitude of the electrosurgical pulse waveform and the second duty cycle to adjust at least one property of the electrosurgical pulse waveform.

In an aspect, the electrosurgical pulse waveform is monophasic to cause neuromuscular stimulation, and the at least one property includes at least one of a repetition frequency or a pulse width period. The repetition frequency of the monophasic electrosurgical pulse waveform is greater than about 100 kHz. In another aspect, the pulse width period is adjusted such that a highest amplitude peak of the monophasic electrosurgical pulse waveform is present from about 500 kHz to about 5 MHz in a frequency domain.

In another aspect, the electrosurgical pulse waveform is biphasic to reduce an amount of an NMBA, and the at least one property includes at least one of a repetition frequency or a pulse width period. The repetition frequency of the biphasic electrosurgical pulse waveform is greater than about 100 kHz. In another aspect, the pulse width period of each cycle of the biphasic electrosurgical pulse waveform is adjusted to be less than about 2 µs.

In yet another aspect, controlling the first and second duty cycles further includes measuring at least one of a tissue property or an energy property and controlling the first and second duty cycles in response to at least one of the tissue property or an energy property.

BRIEF DESCRIPTION OF THE DRAWINGS

The present disclosure may be understood by reference to the accompanying drawings, when considered in conjunction with the subsequent, detailed description, in which.

DETAILED DESCRIPTION

Particular embodiments of the present disclosure are described hereinbelow with reference to the accompanying drawings. In the following description, well-known functions or constructions are not described in detail to avoid obscuring the present disclosure in unnecessary detail.

A generator according to the present disclosure may perform monopolar and/or bipolar electrosurgical procedures, including, but not limited to, cutting, coagulation, ablation, and vessel sealing procedures. The generator may include a plurality of outputs for interfacing with various electrosurgical instruments (e.g., a monopolar or multi-polar instrument (e.g., needles or catheters) for ablation), return electrode, bipolar electrosurgical forceps, footswitch, etc.). Further, the generator includes electronic circuitry configured to generate radio frequency energy specifically suited for various electrosurgical modes (e.g., cut, blend, coagulation, thermal or non-thermal ablation, division with hemostasis, fulguration, spray, etc.) and procedures (e.g., monopolar, bipolar, vessel sealing, treatment of lesions, denervation, etc.). In embodiments, the generator may be embedded, integrated or otherwise coupled to the electrosurgical instruments providing for an all-in-one electrosurgical apparatus.

Figure 1:
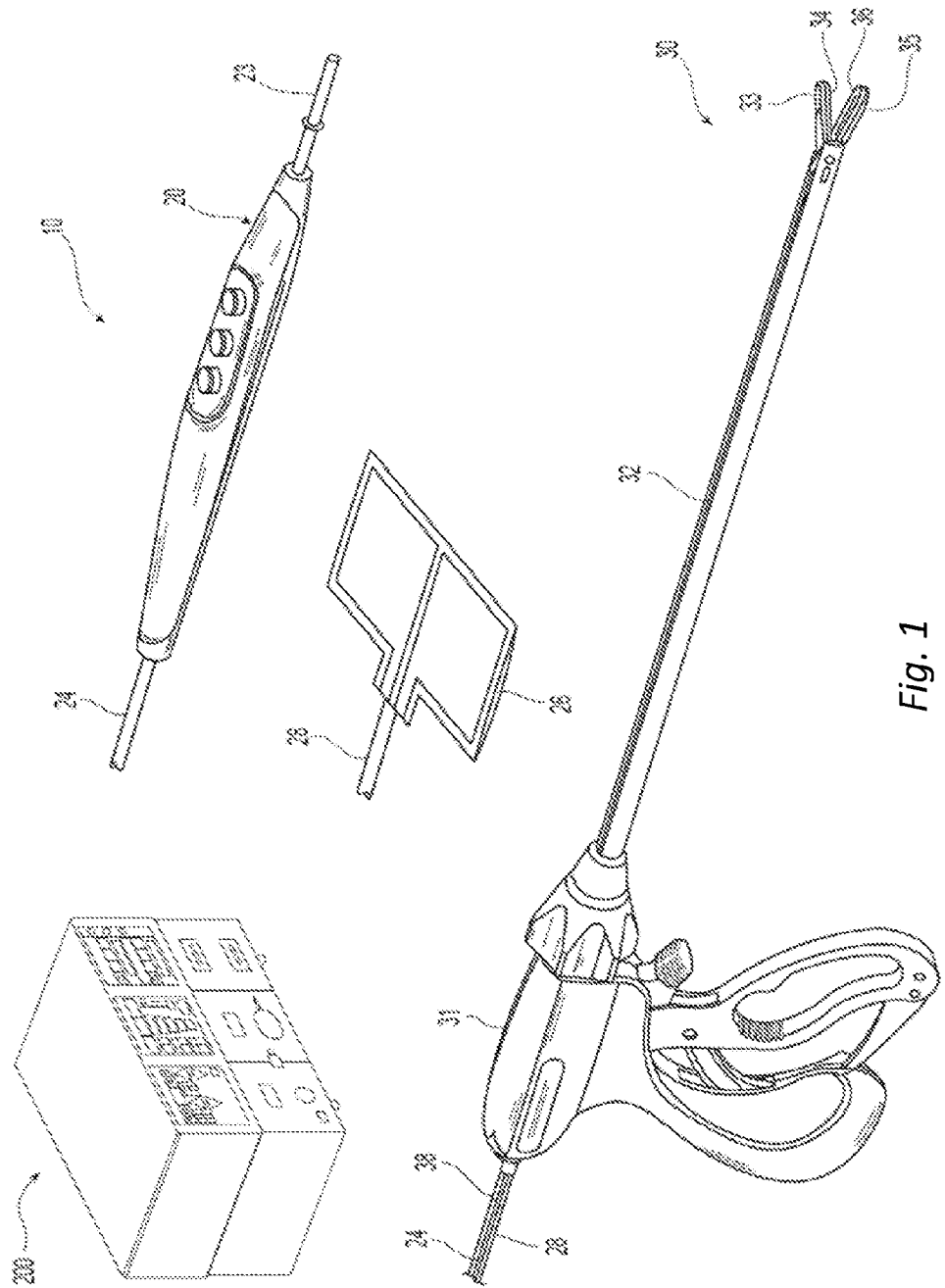
FIG. 1 is a perspective view of an electrosurgical system according to an embodiment of the present disclosure.

FIG. 1 is a perspective view of the components of one illustrative embodiment of a bipolar and monopolar electrosurgical system 10 according to the present disclosure. The system 10 may include one or more monopolar electrosurgical instruments 20 having one or more active electrodes 23 (e.g., electrosurgical cutting probe, ablation electrode(s), etc.) for treating tissue of a patient. Electrosurgical alternating current is supplied to the instrument 20 by a generator 200 via a supply line 24 that is connected to an active terminal 230 (FIG. 3) of the generator 200, allowing the instrument 20 to cut, coagulate, thermally or non-thermally ablate and/or otherwise treat tissue. The alternating current is returned to the generator 200 through a return electrode pad 26 via a return line 28 at a return terminal 232 (FIG. 3) of the generator 200. For monopolar operation, the system 10 may include a plurality of return electrode pads 26 that, in use, are disposed on a patient to minimize the chances of tissue damage by maximizing the overall contact area with the patient. In addition, the generator 200 and the return electrode pads 26 may be configured for monitoring tissue-to-patient contact to ensure that sufficient contact exists therebetween.

Figure 3:
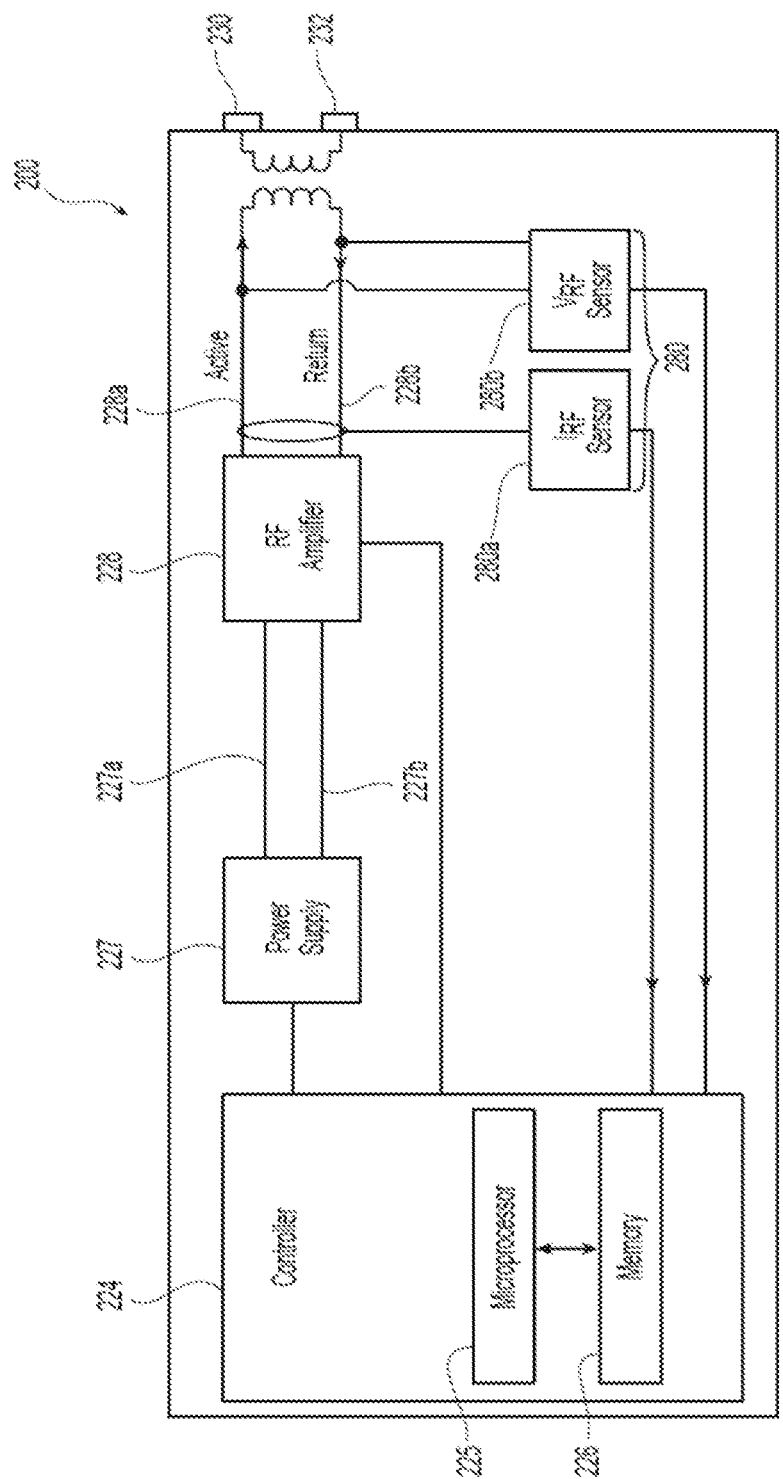
FIG. 3 is a schematic, block diagram of the electrosurgical generator of FIG. 2 according to an embodiment of the present disclosure.

The system 10 may also include one or more bipolar electrosurgical instruments, for example, a bipolar electrosurgical forceps 30 having one or more electrodes for treating tissue of a patient. The electrosurgical forceps 30 includes a housing 31 and opposing jaw members 33 and 35 disposed at a distal end of a shaft 32. The jaw members 33 and 35 have one or more active electrodes 34 and a return electrode 36 disposed therein, respectively. The active electrode 34 and the return electrode 36 are connected to the generator 200 through cable 38 that includes the supply and return lines 24, 28 coupled to the active and return terminals 230, 232, respectively (FIG. 3). The electrosurgical forceps 30 is coupled to the generator 200 at a connector having connections to the active and return terminals 230 and 232 (e.g., pins) via a plug disposed at the end of the cable 38, wherein the plug includes contacts from the supply and return lines 24, 28 as described in more detail below.

Figure 2:
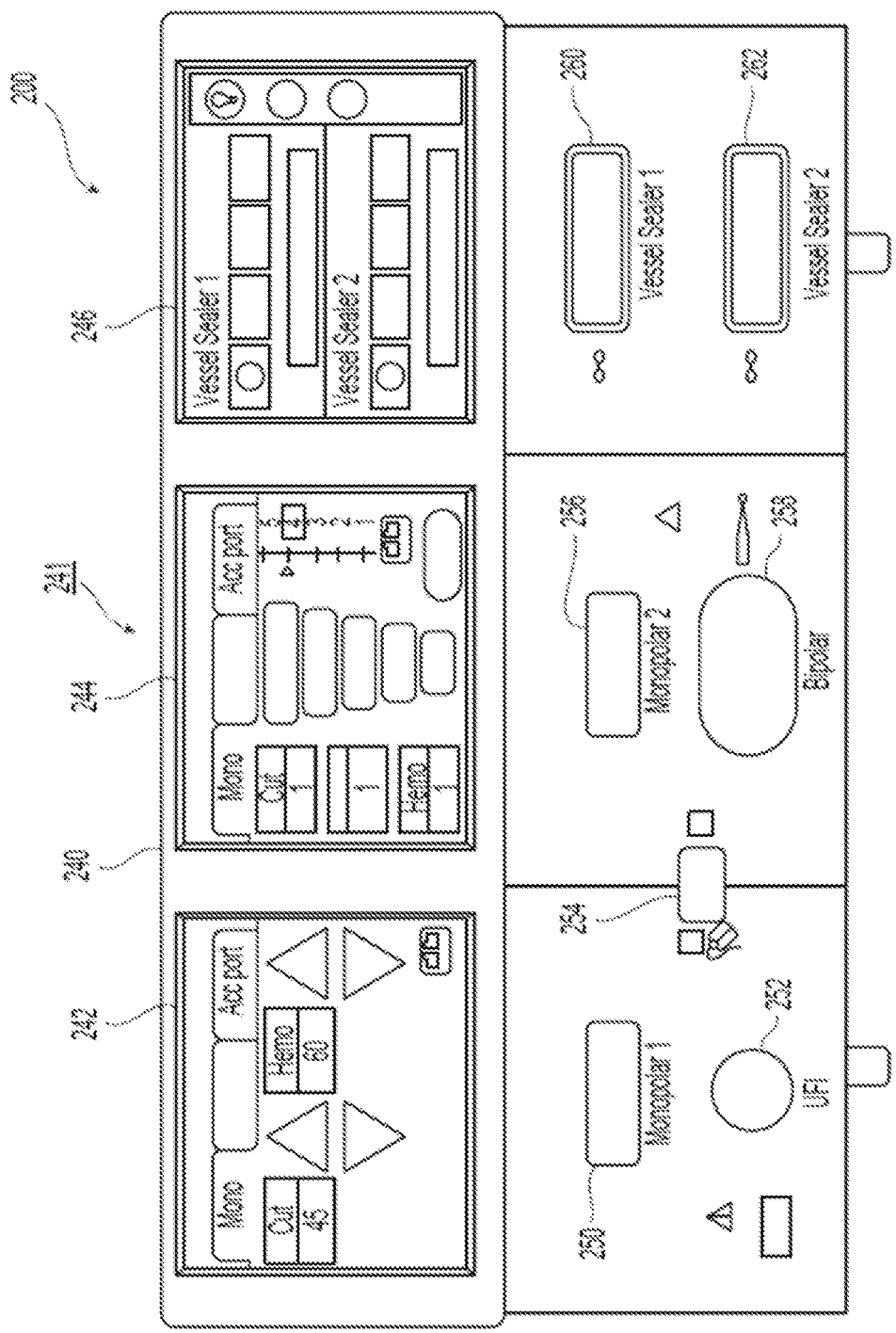
FIG. 2 is a front view of the electrosurgical generator of FIG. 1 according to an embodiment of the present disclosure.

With reference to FIG. 2, a front face 240 of the generator 200 is shown. The generator 200 may be any suitable type (e.g., electrosurgical, microwave, etc.) and may include a plurality of connectors 250-262 to accommodate various types of electrosurgical instruments (e.g., electro surgical forceps 30, etc.).

The generator 200 includes a user interface 241 having one or more display screens or information panels 242, 244, 246 for providing the user with variety of output information (e.g., intensity settings, treatment complete indicators, etc.). Each of the screens 242, 244, 246 is associated with corresponding connector 250-262. The generator 200 includes suitable input controls (e.g., buttons, activators, switches, touch screen, etc.) for controlling the generator 200. The screens of the information panels 242, 244, 246 are also configured as touch screens that display a corresponding menu for the electrosurgical instruments (e.g., electrosurgical forceps 30, etc.). The user then adjusts inputs by simply touching corresponding menu options.

Screen 242 controls monopolar output and the devices connected to the connectors 250 and 252. Connector 250 is configured to couple to a monopolar electrosurgical instrument (e.g., electrosurgical instrument 20) and connector 252 is configured to couple to a foot switch (not shown). The foot switch provides for additional inputs (e.g., replicating inputs of the generator 200). Screen 244 controls monopolar and bipolar output and the devices connected to the connectors 256 and 258. Connector 256 is configured to couple to other monopolar instruments. Connector 258 is configured to couple to a bipolar instrument (not shown).

Screen 246 controls bipolar sealing procedures performed by the electrosurgical forceps 30 that may be plugged into the connectors 260 and 262. The generator 200 outputs energy through the connectors 260 and 262 suitable for sealing tissue grasped by the electrosurgical forceps 30. In particular, screen 246 outputs a user interface that allows the user to input a user-defined intensity setting. The user-defined setting may be any setting that allows the user to adjust one or more energy delivery parameters, such as power, current, voltage, energy, etc. or sealing parameters, such as energy rate limiters, sealing duration, etc. The user-defined setting is transmitted to the controller 224 where the setting may be saved in memory 226. In embodiments, the intensity setting may be a number scale, such as for example, from one to ten or one to five. In embodiments, the intensity setting may be associated with an output curve of the generator 200. The intensity settings may be specific for each electrosurgical forceps 30 being utilized, such that various instruments provide the user with a specific intensity scale corresponding to the electrosurgical forceps 30.

FIG. 3 shows a schematic block diagram of the generator 200 configured to output electrosurgical energy. The generator 200 includes a controller 224, a power supply 227, and a radio-frequency (RF) amplifier 228. The power supply 227 may be a high voltage, DC power supply connected to an AC source (e.g., line voltage) and provides high voltage, DC power to the RF amplifier 228 via leads 227a and 227b, which then converts high voltage, DC power into treatment energy (e.g., electrosurgical or microwave) and delivers the energy to the active terminal 230. The energy is returned thereto via the return terminal 232. The active and return terminals 230 and 232 and coupled to the RF amplifier 228 through an isolation transformer 229. The RF amplifier 228 is configured to operate in a plurality of modes, during which the generator 200 outputs corresponding waveforms having specific duty cycles, peak voltages, crest factors, etc. It is envisioned that in other embodiments, the generator 200 may be based on other types of suitable power supply topologies. RF amplifier 228 may be a non-resonant RF amplifier. A non-resonant RF amplifier, as used herein, denotes an amplifier lacking any tuning components, i.e., conductors, capacitors, etc., disposed between the RF inverter and the load.

The controller 224 includes a processor 225 operably connected to a memory 226, which may include transitory type memory (e.g., RAM) and/or non-transitory type memory (e.g., flash media, disk media, etc.). The processor 225 includes an output port that is operably connected to the power supply 227 and/or RF amplifier 228 allowing the processor 225 to control the output of the generator 200 according to either open and/or closed control loop schemes. A closed loop control scheme is a feedback control loop, in which a plurality of sensors measure a variety of tissue and energy properties (e.g., tissue impedance, tissue temperature, output power, current and/or voltage, etc.), and provide feedback to the controller 224. The controller 224 then controls the power supply 227 and/or RF amplifier 228, which adjusts the DC and/or power supply, respectively. Those skilled in the art will appreciate that the processor 225 may be substituted for by using any logic processor (e.g., control circuit) adapted to perform the calculations and/or set of instructions described herein including, but not limited to, field programmable gate array, digital signal processor, and combinations thereof.

The generator 200 according to the present disclosure includes a plurality of sensors 280, e.g., an RF current sensor 280a, and an RF voltage sensor 280b. Various components of the generator 200, namely, the RF amplifier 228, the RF current and voltage sensors 280a and 280b, may be disposed on a printed circuit board (PCB). The RF current sensor 280a is coupled to the active terminal 230 and provides measurements of the RF current supplied by the RF amplifier 228. The RF voltage sensor 280b is coupled to the active and return terminals 230 and 232 provides measurements of the RF voltage supplied by the RF amplifier 228. In embodiments, the RF current and voltage sensors 280a and 280b may be coupled to active and return leads 228a and 228b, which interconnect the active and return terminals 230 and 232 to the RF amplifier 228, respectively.

The RF current and voltage sensors 280a and 280b provide the sensed RF voltage and current signals, respectively, to the controller 224, which then may adjust output of the power supply 227 and/or the RF amplifier 228 in response to the sensed RF voltage and current signals. The controller 224 also receives input signals from the input controls of the generator 200, the instrument 20 and/or electrosurgical forceps 30. The controller 224 utilizes the input signals to adjust power outputted by the generator 200 and/or performs other control functions thereon.

Figure 4:
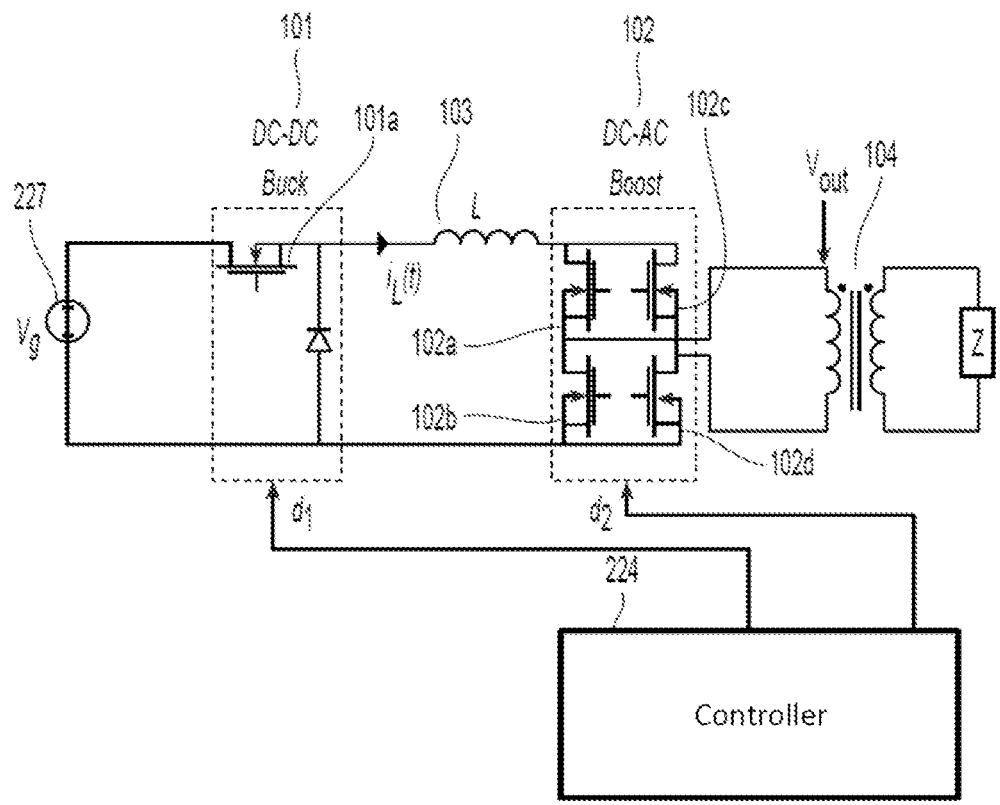
FIG. 4 is a schematic, block diagram of a DC-DC converter and a DC-AC inverter of the electrosurgical generator of FIG. 1 according to an embodiment of the present disclosure.

With reference to the schematic shown in FIG. 4, the generator 200 includes a DC-DC buck converter 101, a DC-AC boost converter 102, an inductor 103, a transformer 104, and controller 224. In embodiments, the DC-AC boost converter 102 is part of each of the RF amplifiers 228a, 228b. Accordingly, for simplicity only one of the RF amplifiers 228a, 228b is discussed herein below. In the exemplary embodiment, a DC voltage source Vg, such as power supply 227, is connected to DC-DC buck converter 101. Furthermore, inductor 103 is electrically coupled between DC-DC buck converter 101 and DC-AC boost converter 102. The output of DC-AC boost converter 102 transmits power to the primary winding of transformer 104, which passes through the secondary winding of transformer 104 to the load Z (e.g., tissue being treated).

DC-DC buck converter 101 includes a switching element 101a and DC-AC boost converter 102 includes a plurality of switching elements 102a-102d arranged in an H-bridge topology. In embodiments, DC-AC boost converter 102 may be configured according to any suitable topology including, but not limited to, half-bridge, full-bridge, push-pull, and the like. Suitable switching elements include voltage-controlled devices such as transistors, field-effect transistors (FETs), combinations thereof, and the like. In an exemplary embodiment, controller 224 is in communication with both DC-DC buck converter 101 and DC-AC boost converter 102, in particular, the switching elements 101a and 102a-102d, respectively. Controller 224 is configured to output control signals, which may be a pulse-width modulated signal, to switching elements 101a and 102a-102d as described in further detail in co-pending application published as US 2014/0254221, entitled CONSTANT POWER INVERTER WITH CREST FACTOR CONTROL, filed on Dec. 4, 2013 by Johnson et al., the entire contents of which is incorporated by reference herein. In particular, controller 224 is configured to control the duty cycle $d_1$ of the control signal supplied to switching element 101a of DC-DC buck converter 101 and duty cycle $d_2$ of the control signals supplied to switching elements 102a-102d of DC-AC boost converter 102. Additionally, controller 224 is configured to measure power characteristics of generator 200, and control generator 200 based at least in part on the measured power characteristics. Examples of the measured power characteristics include the current through inductor 103 and the voltage at the output of DC-AC boost converter 102. In an exemplary embodiment, controller 224 controls buck converter 101 by generating the duty cycle $d_1$ based on a comparison of the inductor current and a nonlinear carrier control current for every cycle.

In an embodiment, generator 200 may generate electrosurgical pulse waveforms that are substantially square as shown in FIGS. 5A-6B. The non-resonant RF amplifiers 228 according to the present disclosure is configured to generate square waveforms due to its non-resonant topology, rather than sine waveforms, which are generated by resonant networks that are absent from the RF amplifier 228. The electrosurgical pulse waveforms of FIGS. 5A-6B are generated by the RF amplifier 228 of the generator 200 at different repetition frequency and/or different pulse width frequency according to embodiments of the present disclosure.

Figure 5A:
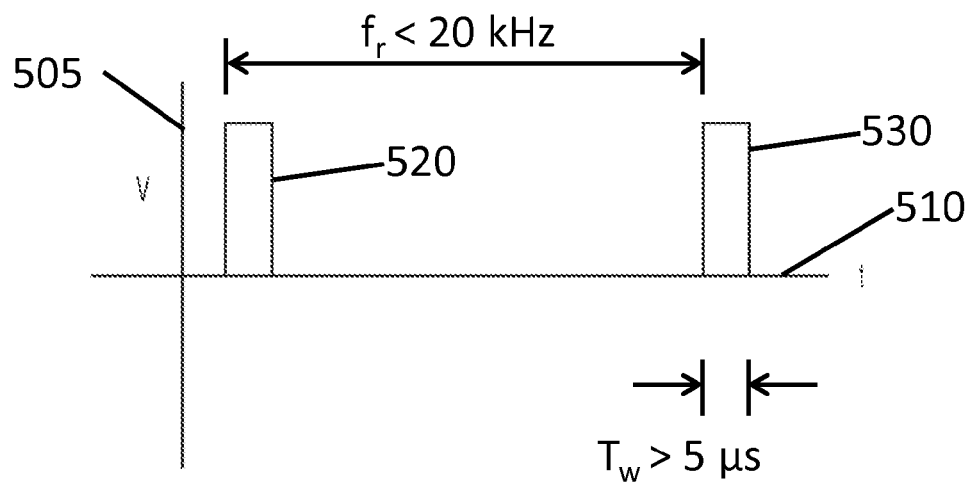
FIGS. 5A and 5B are graphical representations of electrosurgical pulse waveforms generated by the electrosurgical generator of FIG. 1 according to an embodiment of the present disclosure.
Figure 5B:
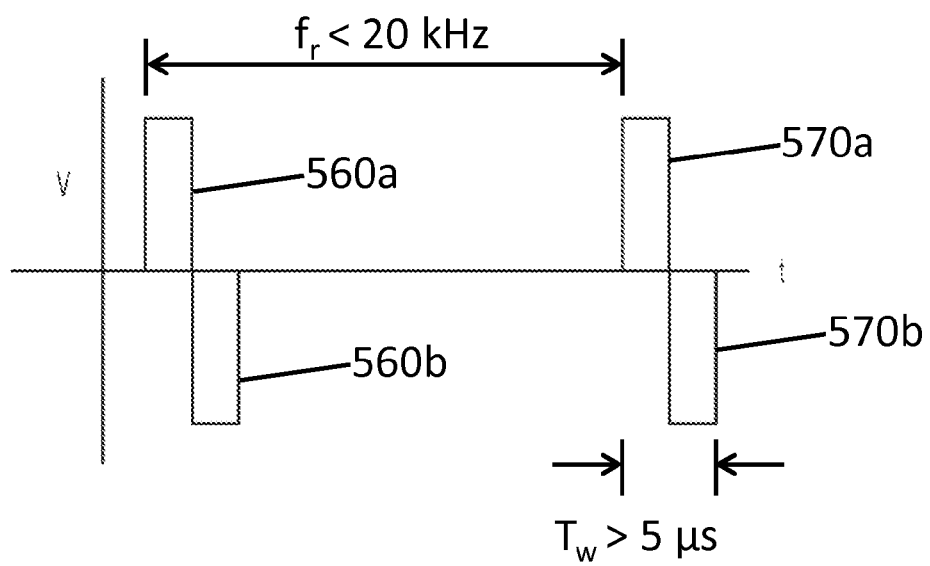

Both FIGS. 5A and 5B show electrosurgical pulse waveforms having a low repetition frequency, which is less than about 20 kHz. In particular, FIG. 5A shows monophasic electrosurgical pulse waveforms 520 and 530 and FIG. 5B shows biphasic electrosurgical pulse waveforms 560a-570b. Since monophasic electrosurgical pulse waveforms 520 and 530 include DC component, monophasic electrosurgical pulse waveforms 520 and 530 may be used to stimulate muscles and nerves or act as a NMSA to identify and locate nerves and muscles during electrosurgical procedures, and the biphasic electrosurgical pulse waveforms 560a-570b may be used to reduce the amount of NMSAs and NMBAs. As such, monophasic electrosurgical pulse waveforms may eliminate the need for NMSAs.

The vertical axis 505 represents amplitude of voltage and the horizontal axis 510 represents time. Repetition time $T_r$ indicates duration of repetition of one full cycle of electrosurgical pulse waveforms. That is, one cycle of a monophasic electrosurgical pulse waveform 520 includes one pulse and that of a biphasic electrosurgical pulse waveform includes two pulses 560a and 560b, where one pulse (e.g., pulse 560a) is upward and the other one (e.g., pulse 560b) is downward. Repetition frequency $f_r$ is the frequency equivalent to the repetition time $T_r$. Pulse width period $T_w$ indicates duration while an electrosurgical pulse waveform is on or maintains a voltage, and pulse width frequency $f_w$ is a frequency equivalent to the pulse width period $T_w$.

Electrosurgical pulse waveforms are generated by the generator 200 based on the control signals $d_1$ and $d_2$. The control signal $d_1$ controls the magnitude of the electrosurgical pulse waveform. Specifically, the control signal $d_1$ controls a duty cycle of the PWM signal to the converter 101. Thus, if the magnitude of the electrosurgical pulse waveform is lower than expected, the control signal $d_1$ increases the duty cycle of the PWM signal. Conversely, if the magnitude of the electrosurgical pulse waveform is higher than expected, the control signal $d_1$ decreases the duty cycle of the PWM signal.

The control signal $d_2$ controls the duty cycle of the PWM control signal as well as other characteristics of the PWM control signal. In an embodiment, the control signal $d_2$ may control switching frequency of the switches 102a-102d and duration that each switch 102a-102d holds its state. The switching frequency is related to the repetition frequency $f_r$ and the duration is related to the pulse width period $T_w$.

As shown in FIGS. 5A and 5B, the repetition frequency $f_r$ is less than about 20 kHz and the pulse width period $T_w$ is greater than about 5 microsecond (μs). Frequency related to 5 μs of the pulse width period is 200 kHz. Thus, electrosurgical energy is present more at the low frequency, which is less than about 20 kHz, than at the high frequency, which is higher than about 200 kHz.

NMSAs have been employed during electrosurgical procedures during which it is desirable to locate or stimulate nerves and muscles. Since muscles or nerves are stimulated at low frequencies, muscles and nerves can also be identified or stimulated by using monophasic or biphasic electrosurgical pulse waveforms, in which more energy is present at a low frequency (e.g., a frequency below about 100 kHz). In this way, monophasic electrosurgical pulse waveforms may eliminate the need for separate NMSAs to locate nerves or stimulate muscles because the monophasic electrosurgical pulse waveforms have DC component, and biphasic electrosurgical pulse waveforms may be used to reduce the amount of NMSAs and NMBAs.

Figure 6A:
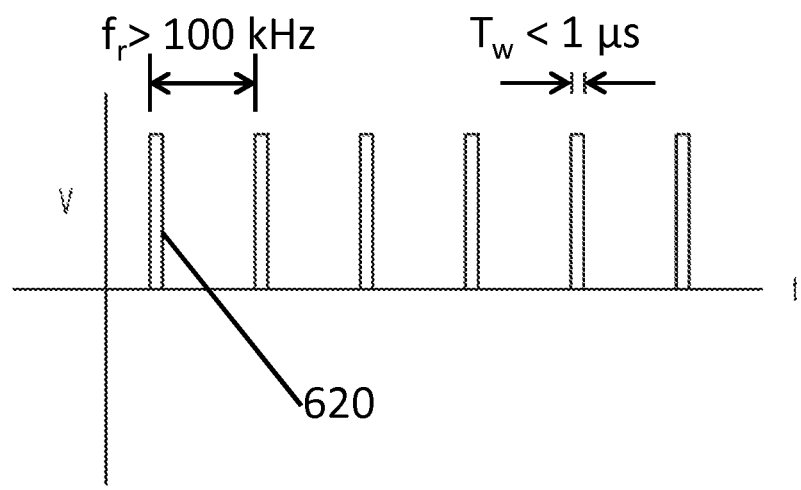
FIGS. 6A and 6B are graphical representations of electrosurgical pulse waveforms generated by the electrosurgical generator of FIG. 1 according to an embodiment of the present disclosure.
Figure 6B:
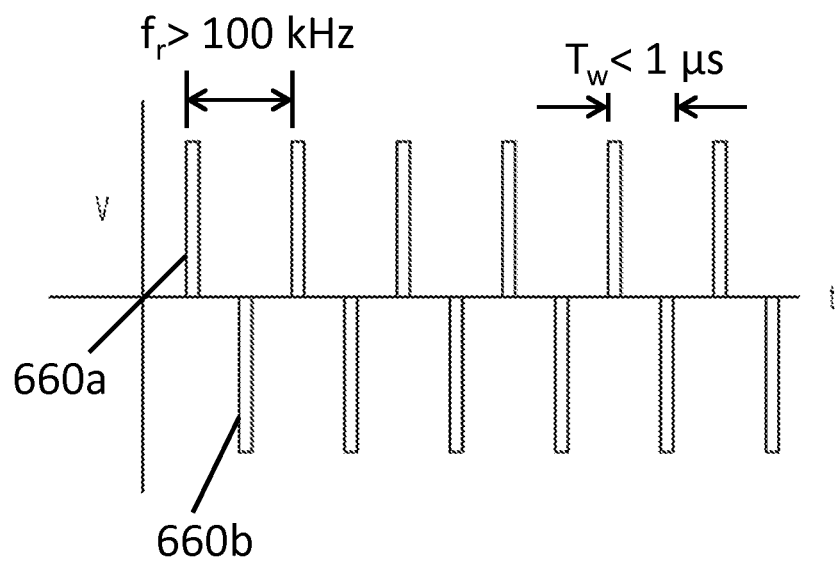

FIGS. 6A and 6B illustrate electrosurgical pulse waveforms having more energy at frequencies greater than about 100 kHz which avoid muscle and nerve stimulation; thus, reducing the need for NMBAs. FIG. 6A shows monophasic electrosurgical pulse waveforms 620 and FIG. 6B shows biphasic electrosurgical pulse waveforms 660a-660b. In both FIGS. 6A and 6B, the repetition frequency $f_r$ is greater than about 100 kHz and the pulse width period $T_w$ is less than about 1 μs. The pulse width period is a period of a full cycle of the upward and downward pulses. In an embodiment, the repetition frequency $f_r$ may be from about 100 kHz to about 500 kHz and the pulse width period $T_w$ may be adjusted to be from about 0.2 μs to 2 μs so that the highest amplitude peak in its energy spectra is present from about 500 kHz to about 5 MHz in the frequency domain.

Electrosurgical energy is present at the repetition frequency $f_r$, which is greater than about 100 kHz, and thus the electrosurgical pulse waveforms do not cause nerve and/or muscle stimulations. Biphasic electrosurgical pulse waveforms may act as interrupt signals interrupting communications between muscles and neurons so that the need for NMBAs is reduced.

In an embodiment, the pulse width period $T_w$ may be adjusted to provide sufficient energy to obtain desired therapeutic effects or purposes. Further, the converter 101 and the inverter 102 are controlled to provide a sufficient energy of the electrosurgical waveforms at a desired frequency.

Figure 7:
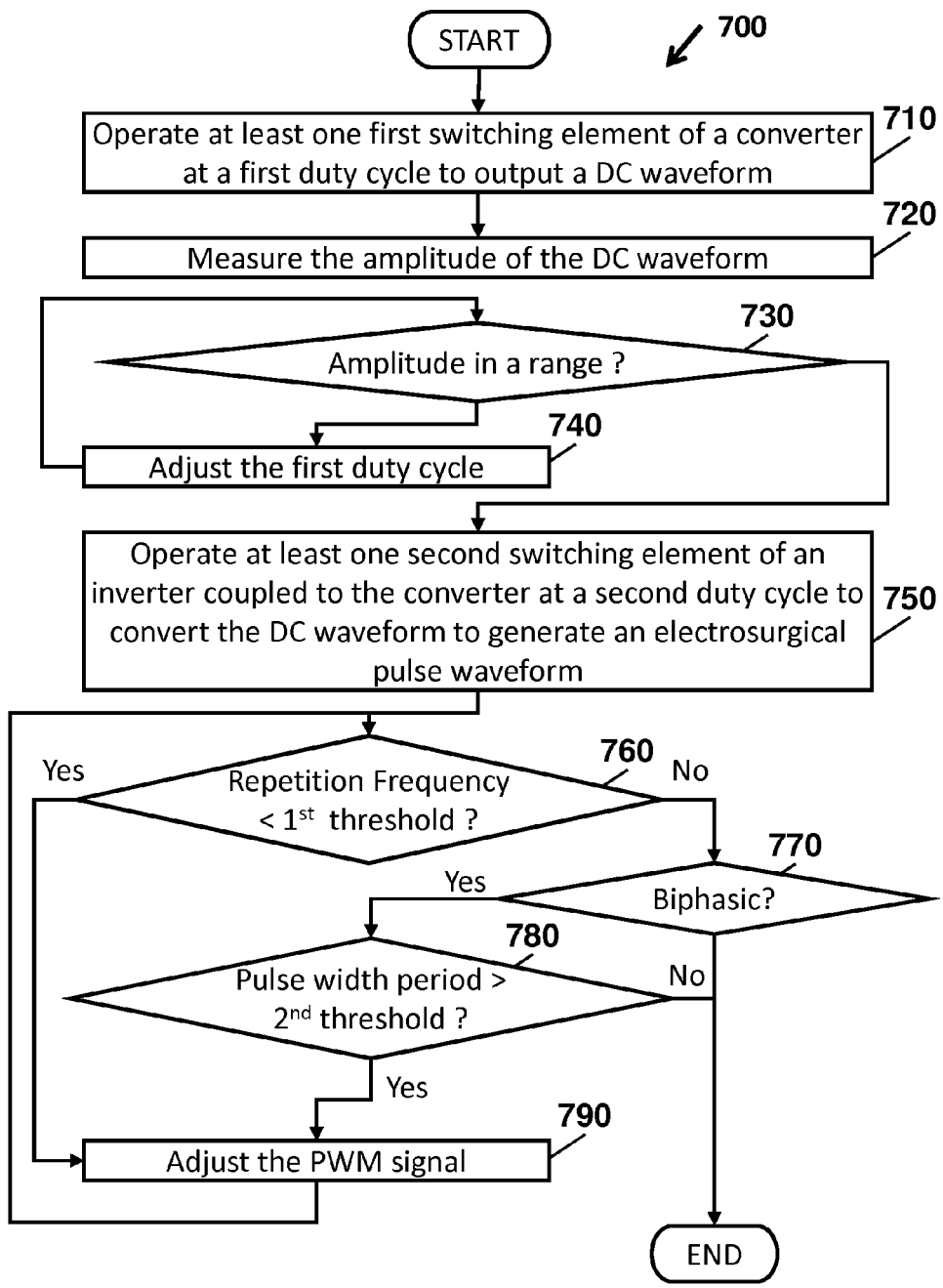
FIG. 7 is a flow chart for controlling the electrosurgical generator of FIG. 1 according to an embodiment of the present disclosure.

FIG. 7 shows a flow chart illustrating a method 700 for controlling the electrosurgical generator 200 of FIG. 1 according to embodiments of the present disclosure. The method 700 may be embodied in software and/or hardware of the electrosurgical generator 200. In embodiments, the controller 224 is configured to control operation of the electrosurgical generator 200 and generation of electrosurgical waveforms according to the present disclosure. In further embodiments, software may include instructions stored in memory 224 and executable by the microprocessor 225.

The method 700 begins with step 710, in which at least one switching element of the converter 101 is operated at a first duty cycle to output a DC waveform and the converter 101 generates DC power with a desired magnitude based on the first duty cycle. In step 720, the amplitude of the DC waveform is measured and in step 730, the generator 200 determines whether the measured amplitude is within a predetermined range.

In an embodiment, the measured amplitude may be amplitude of the current, voltage, or power based on a mode of an electrosurgical operation (e.g., the constant voltage limit mode, the constant current limit mode, the constant power mode, respectively). In another embodiment, the mode of the electrosurgical operation may determine the predetermined range. In a further embodiment, a predetermined range for the constant voltage limit mode may have a different magnitude from that for the constant current limit mode.

When it is determined that the measured amplitude is not within the predetermined range in step 730, the first duty cycle for the converter 101 is adjusted in step 740. In an embodiment, when the measured amplitude is above the predetermined range, the duty cycle is lowered so that measured amplitude is lowered accordingly. Conversely, when the measured amplitude is below the predetermined range, the duty cycle is raised so that measured amplitude is increased accordingly.

When it is determined that the measured amplitude is within the predetermined range in step 730, at least one second switching element of the inverter 102 is operated at a second duty cycle to convert the DC waveform to an electrosurgical pulse waveform in step 750. The energy of the electrosurgical pulse waveform is distributed at several frequencies, which can be controlled or adjusted by the repetition rate and the pulse width frequency. In an embodiment, the control signal (e.g., PWM signal) may be used to adjust the repetition frequency and the pulse width frequency of the electrosurgical pulse waveform to obtain desired waveforms as described above with respect to FIGS. 5A-6B.

In step 760, it is determined whether the repetition frequency of the electrosurgical pulse waveform is less than a first threshold. As shown in FIGS. 6A and 6B, the repetition frequency may be greater than about 100 kHz so that the electrosurgical pulse waveform may not stimulate muscles and/or nerves. When the repetition frequency is less than the first threshold, the PWM signal is adjusted so that the repetition frequency is above the first threshold of step 790.

When it is determined that the repetition frequency is above the first threshold in step 760, it is also determined whether the electrosurgical pulse waveform is biphasic in step 770.

In instances when the electrosurgical pulse waveform is determined to be biphasic, as in step 770, it is also determined whether the pulse width period is below the second threshold as in step 780. The pulse width period may indicate that sufficient electrosurgical energy is provided for an electrosurgical mode of operation. Specifically, the lower the pulse width period, the lower is the electrosurgical energy delivered with each of the electrosurgical pulse waveform. In embodiments, a frequency equivalent to the pulse width period is adjusted to be greater than the repetition frequency and likewise, a frequency equivalent to the second threshold is programmed to be greater than the first threshold. In an embodiment, the repetition frequency may be from about 100 kHz to about 500 kHz and the pulse width period may be adjusted so that the highest amplitude peak in its energy spectra is present from about 500 kHz to about 5 MHz in the frequency domain.

When it is determined that the pulse width period is greater than the second threshold in step 780, the PWM signal is adjusted in step 790 so that the pulse width period becomes less than or equal to the second threshold. In this way, the PWM signal is adjusted by performing steps 760-790 until the repetition frequency is above the first threshold and the pulse width period are less than the second threshold.

By increasing the repetition frequency and/or decreasing the pulse width period, the duty cycle of the electrosurgical waveform is lowered. Conversely, by decreasing the repetition frequency and/or increasing the pulse width period, the duty cycle of the electrosurgical waveform is increased.

When it is determined that the pulse width period is less than the second threshold in step 780, the method 700 is complete. In this way, the electrosurgical pulse waveforms can cause stimulation of muscles and nerves so as to reduce the amount of NMSAs and can reduce the amount of NMSAs or NMBAs, by controlling frequencies of electrosurgical pulse waveforms.

While several embodiments of the disclosure have been shown in the drawings and/or described herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrosurgical generator for minimizing neuromuscular stimulation, comprising:
   a converter configured to output a DC waveform, the converter including at least one first switching element operated via a first pulse-width modulation (PWM) signal;
   an inverter coupled to the converter and including at least one second switching element operated via a second pulse-width modulation (PWM) signal, the inverter configured to invert the DC waveform to generate an electrosurgical pulse waveform; and
   a controller coupled to the converter and the inverter and configured to:
      control a duty cycle of the first PWM signal to adjust a magnitude of the electrosurgical pulse waveform;
      determine whether a repetition frequency of the second PWM signal is above a first threshold;
      determine whether a pulse width of the second PWM signal is greater than a second threshold, when the repetition frequency is determined to be greater than the first threshold; and
      adjust the second PWM signal to adjust at least one property of the electrosurgical pulse waveform, when the pulse width period of the second PWM signal is greater than the second threshold.

2. The electrosurgical generator according to claim 1, wherein the electrosurgical pulse waveform is monophasic to cause neuromuscular stimulation, and
   wherein the at least one property includes at least one of a repetition frequency of the electrosurgical pulse waveform or a pulse width period of the electrosurgical pulse waveform.

3. The electrosurgical generator according to claim 2, wherein the controller is configured to adjust the repetition frequency of the second PWM signal so that a repetition frequency of the monophasic electrosurgical pulse waveform is greater than about 100 kHz.

4. The electrosurgical generator according to claim 2, wherein the controller is configured to adjust the pulse width period of the second PWM signal so that a pulse width period of the electrosurgical pulse waveform is less than about 2 μs.

5. The electrosurgical generator according to claim 1, wherein the electrosurgical pulse waveform is biphasic to reduce an amount of a neuromuscular blocking agent, and
   wherein the at least one property includes at least one of a repetition frequency of the electrosurgical pulse waveform or a pulse width period of the electrosurgical pulse waveform.

6. The electrosurgical generator according to claim 5, wherein the controller is configured to adjust the repetition frequency of the second PWM signal so that a repetition frequency of the biphasic electrosurgical pulse waveform is greater than about 100 kHz.

7. The electrosurgical generator according to claim 5, wherein the controller is configured to adjust the pulse width period of the second PWM signal such that a highest amplitude peak of the biphasic electrosurgical pulse waveform is present from about 500 kHz to about 5 MHz in a frequency domain.

8. The electrosurgical generator according to claim 1, wherein the converter is a buck converter.

9. The electrosurgical generator according to claim 1, wherein the inverter is a boost converter.

10. A method for controlling an electrosurgical generator to minimize neuromuscular stimulation, the method comprising:
operating at least one first switching element of a converter of the electrosurgical generator via a first pulse-width modulation (PWM) signal to output a DC waveform;
operating at least one second switching element of an inverter of the electrosurgical generator via a second pulse-width modulation (PWM) signal to convert the DC waveform to generate an electrosurgical pulse waveform;
controlling a duty cycle of the first PWM signal to adjust a magnitude of the electrosurgical pulse waveform;
determining whether a repetition frequency of the second PWM signal is above a first threshold;
determining whether a pulse width period of the second PWM signal is greater than a second threshold, when the repetition frequency is determined to be greater than the first threshold; and
adjusting the second PWM signal to adjust at least one property of the electrosurgical pulse waveform, when the pulse width period of the second PWM signal is determined to be greater than the second threshold.

11. The method according to claim 10, wherein the electrosurgical pulse waveform is monophasic, and
wherein the at least one property includes at least one of a repetition frequency of the electrosurgical pulse waveform or a pulse width period of the electrosurgical pulse waveform.

12. The method according to claim 11, adjusting the repetition frequency of the second PWM signal so that the monophasic electrosurgical pulse waveform is greater than about 100 kHz.

13. The method according to claim 11, adjusting the pulse width period of the second PWM signal such that a highest amplitude peak of the monophasic electrosurgical pulse waveform is present from about 500 kHz to about 5 MHz in a frequency domain.

14. The method according to claim 10, wherein the electrosurgical pulse waveform is biphasic, and
wherein the at least one property includes at least one of a repetition frequency of the electrosurgical pulse waveform or a pulse width period of the electrosurgical pulse waveform.

15. The method according to claim 14, further comprising adjusting the repetition frequency of the second PWM signal such that the biphasic electrosurgical pulse waveform is greater than about 100 kHz.

16. The method according to claim 14, further comprising adjusting the pulse width period of the second PWM signal such that a pulse width period of each cycle of the biphasic electrosurgical pulse waveform is less than about 2 µs.

17. The method according to claim 10, further comprising:
measuring at least one of a tissue property or an energy property; and
adjusting the first and second PWM signals in response to at least one of the tissue property or the energy property.

18. The electrosurgical generator according to claim 1, wherein the controller is further configured to determine whether the second PWM signal is biphasic.

19. The electrosurgical generator according to claim 18, wherein the controller determines whether the pulse width of the second PWM signal is greater than the second threshold when the second PWM signal is determined to be biphasic.

* * * * *